(12) United States Patent
Ogle et al.

(10) Patent No.: US 6,969,453 B2
(45) Date of Patent: Nov. 29, 2005

(54) SMALL SEPARATION APPARATUS

(75) Inventors: David Ogle, Cowan (AU); Dennis Rylatt, Ryde (AU)

(73) Assignee: Gradipore Limited, Frenchs Forest (AU)

( * ) Notice: Subject to any disclaimer, the term of this patent is extended or adjusted under 35 U.S.C. 154(b) by 517 days.

(21) Appl. No.: 09/837,678

(22) Filed: Apr. 18, 2001

(65) Prior Publication Data

US 2001/0052462 A1 Dec. 20, 2001

(30) Foreign Application Priority Data

Apr. 18, 2000 (AU) .............................................. PQ6973

(51) Int. Cl.[7] ..................... G01N 27/447; G01N 27/453; G01N 7/00
(52) U.S. Cl. ..................... 204/456; 204/606; 204/450; 204/600; 204/518; 204/527; 204/627
(58) Field of Search ................................ 204/456, 450, 204/522, 523, 518, 527, 600, 606, 627, 633, 634, 543, 546

(56) References Cited

U.S. PATENT DOCUMENTS

| | | | |
|---|---|---|---|
| 3,878,564 A | 4/1975 | Yao et al. |
| 4,036,748 A | 7/1977 | Knickel et al. |
| 4,045,337 A | 8/1977 | Knickel et al. |
| 4,045,455 A | 8/1977 | Vogel |
| 4,069,215 A | 1/1978 | Elfert et al. |
| 4,115,225 A | 9/1978 | Parsi |
| 4,123,342 A | 10/1978 | Ahlgren |
| 4,174,439 A | 11/1979 | Rauenbusch et al. |
| 4,196,304 A | 4/1980 | Naumann |
| 4,204,929 A | 5/1980 | Bier |
| 4,217,227 A | 8/1980 | Elfert et al. |
| 4,238,306 A | 12/1980 | Perry et al. |
| 4,238,307 A | 12/1980 | Perry et al. |
| 4,252,652 A | 2/1981 | Elfert et al. |
| 4,259,079 A | 3/1981 | Blum |
| 4,269,967 A | 5/1981 | Elfert et al. |
| 4,276,140 A | 6/1981 | Jain |
| 4,279,724 A | 7/1981 | Hearn et al. |

(Continued)

FOREIGN PATENT DOCUMENTS

| | | | |
|---|---|---|---|
| EP | 0 477 541 B1 | 3/1997 | |
| JP | 03118462 A | * 5/1991 | .......... G01N/27/26 |
| WO | WO 93/06475 | 4/1993 | |
| WO | WO 97/14486 | 4/1997 | |
| WO | WO 98/21384 | 5/1998 | |
| WO | WO 98/36821 | 8/1998 | |
| WO | WO 98/43718 | 10/1998 | |
| WO | PCT/AUO1/00445 | 6/2001 | ........... B01D/57/02 |

OTHER PUBLICATIONS

English language translation of JP 03–118462 A (Murakawa).*

JPO abstract of Murakawa et al. (JP–03118462 A).*

*Primary Examiner*—Alex Noguerola
(74) *Attorney, Agent, or Firm*—Morgan Lewis & Bockius LLP

(57) ABSTRACT

An electrophoresis apparatus for processing compounds in small sample volumes comprising a cathode in a static cathode buffer zone or compartment, an anode in a static anode buffer zone or compartment. The cathode disposed relative to the anode so as to be adapted to generate an electric field in an electric field area therebetween upon application of a voltage potential between the cathode and anode. A removable cartridge disposed in the electric field area between the anode and the cathode. The cartridge containing a first non-isoelectric separation barrier and also a second non-isoelectric separation barrier disposed between a selected one of the cathode buffer zone and the anode buffer zone and the first barrier so as to define a first chamber having an interstitial volume of less than 5 ml therebetween.

45 Claims, 11 Drawing Sheets

U.S. PATENT DOCUMENTS

| | | |
|---|---|---|
| 4,299,677 A | 11/1981 | Venkatasubramanian et al. |
| 4,322,275 A | 3/1982 | Jain |
| 4,362,612 A | 12/1982 | Bier |
| 4,376,023 A | 3/1983 | Venkatsubramanian et al. |
| 4,381,232 A | 4/1983 | Brown |
| 4,383,923 A | 5/1983 | Elfert |
| 4,396,477 A | 8/1983 | Jain |
| 4,441,978 A | 4/1984 | Jain |
| 4,533,447 A | 8/1985 | Meldon |
| 4,608,140 A | 8/1986 | Goldstein |
| 4,661,224 A | 4/1987 | Goldstein et al. |
| 4,673,483 A | 6/1987 | Mandle |
| 4,711,722 A | 12/1987 | Toyoshi et al. |
| 4,746,647 A | 5/1988 | Svenson |
| 4,780,411 A | 10/1988 | Piejko et al. |
| 4,897,169 A | 1/1990 | Bier et al. |
| 4,963,236 A | 10/1990 | Rodkey et al. |
| 5,043,048 A | 8/1991 | Muralidhara |
| 5,080,770 A | 1/1992 | Culkin |
| 5,082,548 A | 1/1992 | Faupel et al. |
| 5,087,338 A | 2/1992 | Perry et al. |
| 5,096,547 A | 3/1992 | Klotz et al. |
| 5,114,555 A | 5/1992 | Stimpson |
| 5,127,999 A | 7/1992 | Klotz et al. |
| 5,160,594 A | 11/1992 | Huff et al. |
| 5,173,164 A | 12/1992 | Egen et al. |
| 5,185,086 A | 2/1993 | Kaali et al. |
| 5,238,570 A | 8/1993 | Hugl et al. |
| 5,256,269 A | 10/1993 | Sova |
| 5,277,774 A | 1/1994 | Shmidt et al. |
| 5,336,387 A | 8/1994 | Egen et al. |
| 5,340,449 A | 8/1994 | Shukla |
| 5,352,343 A | 10/1994 | Bailes et al. |
| 5,407,553 A | 4/1995 | Herron et al. |
| 5,420,047 A | 5/1995 | Brandt et al. |
| 5,437,774 A | 8/1995 | Laustsen |
| 5,441,646 A | 8/1995 | Heller et al. |
| 5,490,939 A | 2/1996 | Gerigk et al. |
| 5,503,744 A | 4/1996 | Ikematsu et al. |
| 5,504,239 A | 4/1996 | Mehl et al. |
| 5,558,753 A | 9/1996 | Gallagher et al. |
| 5,561,115 A | 10/1996 | Tenold |
| 5,565,102 A | 10/1996 | Brandt et al. |
| 5,610,285 A | 3/1997 | Lebing et al. |
| 5,662,813 A | 9/1997 | Sammons et al. |
| 5,723,031 A | 3/1998 | Durr et al. |
| 5,733,442 A | 3/1998 | Shukla |
| 5,736,023 A | 4/1998 | Gallagher et al. |
| 5,868,938 A | 2/1999 | Bomer et al. |
| 5,891,736 A | 4/1999 | Chapoteau et al. |
| 5,906,724 A | 5/1999 | Sammons et al. |
| 5,938,904 A | 8/1999 | Bader et al. |
| 5,986,075 A | 11/1999 | DuBose et al. |
| 6,093,296 A | 7/2000 | Soane et al. |
| 6,117,297 A | 9/2000 | Goldstein |
| 6,129,842 A | 10/2000 | Kostanian |
| 6,171,825 B1 | 1/2001 | Chan et al. |
| 6,638,408 B1 * | 10/2003 | Speicher et al. ............ 204/458 |

* cited by examiner

US 6,969,453 B2

SMALL SEPARATION APPARATUS

BACKGROUND OF THE INVENTION

This invention relates to an electrophoretic separation apparatus and in particular, to apparatus for treatment or separation of compounds including macromolecules in small volumes.

In the past, the separation of macromolecular solutes was performed by a process known as electrophoretic separation or electrophoresis, in particular, fixed boundary electrophoretic separation. In fixed boundary electrophoresis, a semi-permeable membrane (hereinafter referred to as a separation membrane), acts to separate two streams of liquid carrying macromolecular solutes such as proteins, known as the sample and the downstream. The streams flow between charged electrodes and at least one macromolecular solute migrates across the membrane from one stream to the other stream under the influence of the electric field. The apparatus also includes flow paths for buffer solutions and further semi-permeable membranes, hereinafter referred to as restriction membranes, disposed either side of the separation membrane between the electrodes and the separation membrane to separate the buffer flow paths from the sample and downstream. The restriction membranes allow the passage of ions but not of the relatively larger macromolecules.

Attempts have been made to improve upon such fixed boundary electrophoresis technology. In particular, one such improvement provided a system in which the separation and restriction membranes and sample and separation are contained in a removable and replaceable cartridge. Although this technology provides a substantial improvement, electrophoresis cannot satisfactorily be used for separating very small samples. Even an apparatus of reduced size is unable to separate very small samples, with the smallest practicable sample size being around 6 mL. Therefore, for smaller samples, other separation methods such as chromatography or gel electrophoresis, have to be used. However, such other methods are time consuming. For example, in gel electrophoresis, the separation in the gel is very slow, taking several hours and further time is wasted in subsequently extracting (eluting) the separated molecules from the gel. A further problem arises in that molecules tend to elongate and denature when separated in a gel in comparison with a zonal electrophoresis separation.

Earlier electrophoretic separation apparatus and methods have been developed for processing large sample volumes and are not suitable to treat small volumes. Furthermore, the ratio of sample to electrophoresis membrane surface area is usually greater than 2.5 mL/cm$^2$, typically around 5 mL/cm$^2$, which results in large dead volumes and the need to re-circulate buffers and samples to reduce heating and prevent clogging of membranes and other separation media.

The present invention seeks to alleviate these problems and in particular, to provide a separation apparatus and methods suitable for use with relatively small sample volumes.

SUMMARY OF THE INVENTION

In accordance with the present invention, there is provided a separation apparatus and methods suitable for use with relatively small sample volumes and can effectively and efficiently separate selected products from such small sample volumes.

Further, in accordance with the present invention, there is provide an apparatus for processing compounds in small volumes by electrophoretic separation, the apparatus comprising:

(a) a cathode in a static cathode buffer zone;

(b) an anode in a static anode buffer zone, the anode disposed relative to the cathode so as to be adapted to generate an electric field in an electric field area therebetween upon application of a voltage potential between the cathode and anode;

(c) a first separation barrier disposed in the electric field area;

(d) a second separation barrier disposed between a selected one of the cathode buffer zone and the anode buffer zone and the first barrier so as to define a first interstitial volume therebetween;

wherein in use, electrophoretic buffer is disposed in the cathode buffer zone and the anode buffer zone, a sample constituent is provided to the first interstitial volume; wherein upon application of the voltage potential, a selected separation product is removed from the sample constituent through a selected one of the first and second separation barriers, and provided to a selected one of the cathode buffer and anode buffer zones; and wherein there is substantially no circulation of buffer or sample constituent in the buffer zones or the first interstitial volume.

Still further, in accordance with the present invention, there is provided an apparatus for processing compounds in small volumes by electrophoretic separation, the apparatus comprising:

(a) a cathode in a static cathode buffer zone;

(b) an anode in a static anode buffer zone, the anode disposed relative to the cathode so as to be adapted to generate an electric field in an electric field area therebetween upon application of a voltage potential between the cathode and anode;

(c) a first separation barrier disposed in the electric field area;

(d) a second separation barrier disposed between the cathode buffer zone and the first barrier so as to define a first interstitial volume therebetween;

(e) a third separation barrier disposed between the anode buffer zone and the first barrier so as to define a second interstitial volume therebetween;

wherein in use, electrophoretic buffer is disposed in the cathode buffer zone, the anode buffer zone and at least one of the first interstitial and second interstitial volumes, a sample constituent is provided to a selected one of the first interstitial and second interstitial volumes; wherein upon application of the voltage potential, a selected separation product is removed from the sample constituent, through the first separation barrier, and provided to the other of the first interstitial and second interstitial volumes; and wherein there is substantially no circulation of buffer or sample constituent in the buffer zones, the first interstitial volume or the second interstitial volume.

Preferably, the small volume is less than about 5 mL, preferably about 2 mL or less. The invention is particularly suitable for separating or processing samples of about 0.02 mL to about 0.1 mL.

A ratio of sample to membrane surface area of less that about 1 mL/cm$^2$ is useful for the present invention. Preferably, the ratio is about 0.5 mL/cm$^2$ or less, more preferably the ratio is about 0.1 mL/cm$^2$ or less, and more preferably about 0.02 mL/cm$^2$.

Through out this specification, the term "buffer" has been used which is intended to include solutions of electrolytes. It will be appreciated that any solution or solvent containing an electrolyte would fall within the definition of "buffer" for the present application. Importantly, the buffer must be a solution which can conduct electricity. Preferably, the solution of electrolytes or buffers used for the present invention have some buffering capacity characteristic of traditional buffers.

An advantage of the present invention is the separation apparatus effectively and efficiently separates selected products from small sample volumes.

Another advantage of the present invention is the ability to load very small samples and carry out fast separations without significant loss of the sample or undue dilution of the samples.

Another advantage of the present invention is the ability to carry out dialysis on very small samples.

These and other advantages and benefits of the invention will be apparent to those skilled in the art upon reading and understanding of the following detailed description.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

DETAILED DESCRIPTION OF THE PREFERRED EMBODIMENTS

Figure 1:
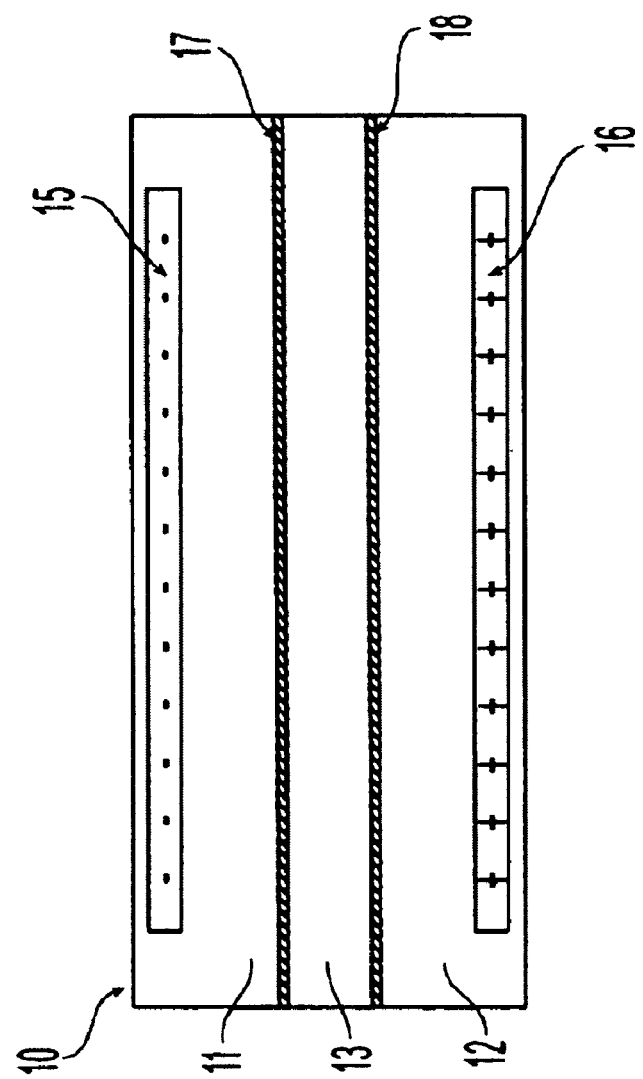
FIG. 1 is a schematic drawing illustrating the basic principal of the first aspect of the present invention having two membranes.

Before describing the preferred embodiments in detail, the principal of operation of the apparatus will first be described. An electric field applied to charged molecules including macromolecules such as proteins in solution will cause the molecules to move to one of the electrodes. If the compound has a positive charge, it will move to the negative electrode (cathode). Conversely, a negatively-charged compound will move to the positive electrode (anode).

In the apparatus of the present invention for separating compounds, an electrophoretic separation membrane is placed in an electric field and compounds are selectively transported between the sample and the separation chambers. The particular separation membrane used will vary for different applications and generally has a relatively large, but well defined, pore size. The sample and separation chambers are isolated from the electrodes by two restriction membranes. Depending on the type of restriction membranes used, the restriction membranes preferably allow the movement of relatively small molecules and ions up to a molecular mass of about 3,000 Dalton.

There are four modes of operating the apparatus of the present invention, namely charge-based separation, charge and size-based separation, concentration, and dialysis and which are discussed below Charge-based Separation In principal, any two compounds with different pI (isoelectric point) values can be separated by carrying the separation out at a pH between the two pI values. The pI is the pH of a solution in which the compound has neutral charge, thus by changing the pH of the solution in which a compound is present, the effective charge of that compound can be changed.

Thus, in a solution with a pH between the two pI values, one compound will have a positive charge, and will move towards the cathode and be contained in the sample chamber. The other compound will have a negative charge and will moved to the separation chamber as it moves towards the anode through the separation membrane.

Charge- and Size-based Separation

Components with different molecular masses can be separated on the basis of pore size of the separation membrane. Two compounds which are both negatively charged but have different molecular masses can be separated because the larger compound is unable to migrate through the smaller pores of the separation membrane. Careful combination of pore size and pH can often allow the isolation of a single component from a complex mixture in one electrophoresis run.

Concentration

Concentration method utilises a large pore size separation membrane (1,000 kDa). The large pore sizes enable the rapid transportation of compounds across the separation membrane from a large volume sample solution to a small volume separation solution. The membrane prevents the excess movement of solute therefore providing desired concentration effect. In this process, a pH is selected in which all of the desired compounds will have the same charge. Typically, pH 8.3 is selected since most proteins will have a negative charge at this pH. In many applications, purification can be achieved at the same time as concentration.

Dialysis

Dialysis also known as de-salting and the apparatus according to the present invention can also be used for method. The separation membrane is not necessary for dialysis, which can be performed with or without this membrane. The ions are removed from the sample by passing through the restriction membranes and then are diluted in the outer electrode compartments. This process also occurs during standard fractionation or concentration, but in these cases the ions are re-circulated. When being used for extensive dialysis, the buffer where the ions collect should preferably be exchanged for fresh buffer solution at regular intervals to maintain acceptable dialysis.

In a first aspect, the present invention provides an apparatus for processing compounds in small volumes by electrophoretic separation, the apparatus comprising:

(a) a cathode in a static cathode buffer zone;

(b) an anode in a static anode buffer zone, the anode disposed relative to the cathode so as to be adapted to generate an electric field in an electric field area therebetween upon application of a voltage potential between the cathode and anode;

(c) a first separation barrier disposed in the electric field area;

(d) a second separation barrier disposed between a selected one of the cathode buffer zone and the anode buffer zone and the first barrier so as to define a first interstitial volume therebetween;

wherein in use, electrophoretic buffer is disposed in the cathode buffer zone and the anode buffer zone, a sample constituent is provided to the first interstitial volume; wherein upon application of the voltage potential, a selected separation product is removed from the sample constituent through a selected one of the first and second separation barriers, and provided to a selected one of the cathode buffer and anode buffer zones; and wherein there is substantially no circulation of buffer or sample constituent in the buffer zones or the first interstitial volume.

For convenience, the cathode and anode buffer zones are also called cathode or anode compartments or the electrode compartments in the present the specification.

The first interstitial volume is also called the sample chamber in the present specification as a convenient reference term.

Preferably, the small volume is less than about 5 mL, preferably about 2 mL or less. The invention is particularly suitable for separating or processing samples of about 0.02 mL to about 0.1 mL.

A ratio of sample to membrane surface area of less that about 1 mL/cm$^2$ is useful for the present invention. Preferably, the ratio is about 0.5 mL/cm$^2$ or less, more preferably the ratio is about 0.1 mL/cm$^2$ or less, and more preferably about 0.02 mL/cm$^2$.

The first and second separation barriers or membranes are suitably electrophoresis separation membranes having a defined pore size, restriction membranes which allow flow of ions into and out of a chamber or compartment under the influence of an electric field but do not allow movement of macromolecules, or a combination of a separation membrane and a restriction membrane.

The separation membranes are preferably ion-permeable electrophoresis separation membranes made from polyacrylamide and having a molecule mass cut-off from about 1 kDa to about 1500 kDa. The molecular mass cut-off of the separation membrane will depend on the sample being processed and the other molecules in the mixture.

The restriction barriers or membranes are preferably formed from polyacrylamide and have a molecular mass cut-off less than the separation membrane, preferably from about 1 kDa to about 1500 kDa. The molecular mass cut-off of the restriction membrane will depend on the sample being processed and the size of the small macromolecules to be removed.

The molecular mass cut-off of the restriction membranes are preferably less than the molecular mass cut-off of the separation membrane. In some circumstances, particularly when very large compounds are being processed, the molecular mass cut-off of the restriction membranes is the same as the molecular mass cut-off of the separation membrane.

The membranes are suitably composed of ultrafiltration, electrodialysis haemodialysis material, electrophoresis materials, or combinations or mixtures thereof. The pore size of an filtration membrane is selected according to the size of the compound to be separated such that the compound cannot pass through the membrane. Typically, the molecular mass cut-off of a filtration membrane if used is between about 100 Da to about 5000 Da.

The apparatus is preferably connected in series so as to carry out a number of treatments of compounds simultaneously.

The first and second membranes are suitably configured in a separation module which is adapted to be removable from a buffer tank which houses the electrodes and electrophoresis buffer(s). When the module is placed in the tank, the cathode and anode buffer chambers are formed. The removable module may include handles for ease of removal or placement.

In one preferred form, the apparatus comprises a plurality of sample chambers positioned between the cathode and anode compartments.

In another preferred form, the apparatus comprises a plurality of cathode and anode compartments each having respective cathode and anode positioned therein together with a plurality of sample chambers positioned between respective pairs of cathode and anode compartments.

The apparatus according to the first aspect of the present invention is particularly adapted for use in dialysing or de-salting samples. In this embodiment, the first and second membranes are restriction membranes.

In use, a sample containing one or more compounds is added to the sample chamber and a voltage potential is applied to cause movement of salts and small molecular mass contaminants through the membranes into the electrophoresis buffer compartments.

In a second aspect, the present invention provides an apparatus for processing compounds in small volumes by electrophoretic separation, the apparatus comprising:

(a) a cathode in a static cathode buffer zone;

(b) an anode in a static anode buffer zone, the anode disposed relative to the cathode so as to be adapted to generate an electric field in an electric field area therebetween upon application of a voltage potential between the cathode and anode;

(c) a first separation barrier disposed in the electric field area;

(d) a second separation barrier disposed between the cathode buffer zone and the first barrier so as to define a first interstitial volume therebetween;

(e) a third separation barrier disposed between the anode buffer zone and the first barrier so as to define a second interstitial volume therebetween;

wherein in use, electrophoretic buffer is disposed in the cathode buffer zone, the anode buffer zone and at least one of the first interstitial and second interstitial volumes, a sample constituent is provided to a selected one of the first interstitial and second interstitial volumes; wherein upon application of the voltage potential, a selected separation product is removed from the sample constituent, through the first separation barrier, and provided to the other of the first interstitial and second interstitial volumes; and wherein there is substantially no circulation of buffer or sample constituent in the buffer zones, the first interstitial volume or the second interstitial volume.

For convenience, the cathode and anode buffer zones are also called cathode or anode compartments or the electrode compartments in the present the specification.

The first interstitial volume is also called the sample chamber in the present specification as a convenient reference term. The second interstitial volume is also called the separation chamber in the present specification as a convenient reference term.

Preferably, the first separation barrier or membrane is an electrophoresis membrane having a defined pore size and the second and third separation barrier or membranes are restriction membranes which allow flow of ions into and out of a chamber or compartment under the influence of an electric field Preferably, the small volume is less than about 5 mL, preferably about 2 mL or less. The invention is particularly suitable for separating samples of about 0.02 mL to about 0.1 mL.

A ratio of sample to separation membrane surface area of less that about 1 mL/cm² is required for the present invention. Preferably, the ratio is about 0.5 mL/cm² or less, more preferably the ratio is about 0.1 mL/cm². or less, and more preferably about 0.02 mL/cm².

In a preferred form, the first, second and third membranes are configured in a separation module which is adapted to be removable from a buffer tank which houses the electrodes and electrophoresis buffer(s). When the module is placed in the tank, the cathode and anode compartments are formed. The removable module may include handles for ease of removal or placement.

In another preferred form, the apparatus comprises a plurality of sample chambers and separation chambers positioned between the cathode and anode compartments.

In another preferred form, the apparatus comprises a plurality of cathode and anode compartments each having respective cathode and anode positioned therein together with a plurality of sample chambers and separation chambers positioned between respective pairs of cathode and anode compartments.

In a preferred embodiments, upper parts of the chambers are wider than lower parts of the chambers for ease of loading the sample.

Separation membranes are preferably ion-permeable electrophoresis separation membranes made from polyacrylamide and having a molecule mass cut-off from about 1 kDa to about 1500 kDa. The molecular mass cut-off of the separation membrane will depend on the sample being processed and the other molecules in the mixture.

Restriction membranes are preferably formed from polyacrylamide and have a molecular mass cut-off less than the separation membrane, preferably from about 1 kDa to about 1500 kDa. The molecular mass cut-off of the restriction membrane will depend on the sample being processed and the size of the small macromolecules to be removed.

The molecular mass cut-off of the restriction membranes are preferably less than the molecular mass cut-off of the separation membrane. In some circumstances, particularly when very large compounds are being processed, the molecular mass cut-off of the restriction membranes is the same as the molecular mass cut-off of the separation membrane.

The membranes are suitably composed of ultrafiltration, electrodialysis haemodialysis material, or electrophoresis materials or combinations or mixtures thereof. The pore size of an filtration membrane is selected according to the size of the compound to be separated such that the compound cannot pass through the membrane. Typically, the molecular mass cut-off of a filtration membrane if used is between about 100 Da to 5000 Da.

In a particularly preferred embodiment of the first and second aspects of the present invention, the compartments and chambers are formed with an open top in use with the membranes oriented substantially vertically and the electric field passing generally horizontally from one electrode to another so that the sample and buffers can be simply and easily loaded into the respective chambers and compartments from above. This arrangement is particularly advantageous in terms of the ease of use of the apparatus.

Surprisingly, it has been found that it is possible to conduct electrophoresis and other similar separation methods such as dialysis, de-salting utilising static small sample volumes, without re-circulation or flow of the samples which was previously thought necessary in order to achieve a good separation. Other methods and apparatus require re-circulation or mixing to cool the sample to prevent overheating and consequent denaturing or destruction of macro molecules in the sample. It has been discovered by the present inventors that with small sample volumes and apparatus adapted to take small volumes, a "static" separation without re-circulation, is accomplished satisfactorily and beneficially, in a surprisingly short period of time.

Typically, dialysis or separation of compounds is achieved in less than about 5 minutes. Good separation or treatment of samples is achieved in about 1 minute.

The apparatus according the present invention is adaptable for analytical work, particularly in research laboratories. The apparatus is suitably either reused or is disposable. When a separation modules is used, the buffer tank can be reused while the module is disposed after use. As very small volumes can be treated with dilute amounts of compounds present, a disposable unit would be beneficial to prevent contamination of samples.

Voltage and/or current applied vary depending on the separation. Typically up to many hundred volts are suitably used but choice and variation of voltage will depend on the configuration of the apparatus, buffers and the sample to be separated or treated. In a laboratory scale instrument, the preferred voltage is about 250 V.

The distance between the electrodes can have an effect on the separation or movement of compounds through the membranes. It has been found that the shorter the distance between the electrodes, the faster the electrophoretic movement of compounds or salts. The effect of the electric field is based on the equation:

$$e = V/d$$

(e=electric field, V=voltage, d=distance)

Therefore, the smaller the distance between the electrodes the better or faster the separation. Preferably, the distance between the electrodes should decrease in order to increase electric field strength, thereby further improving transfer or separation rates. As the apparatus according to the present invention is used for small volumes, the distance between the membranes is preferably about 1 mm, with rapid movement of compounds achieved without undue heating. The result is that there is no substantial adverse affect on properties of the compounds to be treated or separated.

Solvents, in the form of buffers that have been found to be particularly suitable for the method according to the present invention are Tris Borate having a pH around 9.0. It will be appreciated, however, that other buffers or solvents would also be suitable, depending on the separation. The concentration of the selected buffers also influence or effect the movement of micromolecules through the separation barrier. Typically concentrations of about 10 mM to about 200 mM, more preferably about 20 mM to about 80 mM, have been found to be particularly suitable. Almost any buffers and/or solvents can be used with the present invention. The buffers and/or solvents that are used are procedure/method/separation dependent. The concentration of the buffer and/or solvent is dependent upon the application/separation/procedure.

In use, a sample containing one or more compounds is added to the sample chamber and a voltage or electric potential is applied to cause movement of at least one compound from the sample through the separation membrane into the separation chamber while the restriction membranes prevent movement of compounds from the sample chamber into the electrode compartments.

The apparatus is suitably used at room temperature or placed in a controlled temperature environment like a cool room in order to ensure that compounds to be treated or separated are not unduly heated prior, during or after electrophoresis.

In a third aspect, the present invention provides a method for de-salting or dialysing a small volume sample containing at least one compound, the method comprising:

(a) providing an apparatus according to the first aspect of the present invention;

(b) adding buffer to the cathode and anode compartments or zones (c) placing a sample in a sample chamber of the apparatus; and (d) applying an electric field to the sample in the sample chamber such that salts in the sample move to the buffer in the electrode buffer compartments while the at least one compound is substantially retained in the sample chamber, wherein there is substantially no re-circulation of liquid in the sample chamber or buffer in the buffer compartments.

Preferably, the small volume is less than about 5 mL, preferably about 2 mL or less. The invention is particularly suitable for separating samples of about 0.02 mL to about 0.1 mL.

The membranes allow the movement of ions and small molecular weight compounds but do not allow the movement of the one or more compounds to be de-salted or dialysed.

In a fourth aspect, the present invention provides a method of separating a compound in small volumes of solution by electrophoresis, the method comprising:

(a) providing an apparatus according to the second aspect of the present invention;

(b) adding buffer to the cathode and anode compartments or zones and to at least one of the interstitial volumes or separation chambers;

(c) adding a sample to a sample chamber of the apparatus;

(d) applying an electrical potential between the electrodes in the electrode compartments causing at least one compound type to transfer across the separation membrane to a separation chamber, wherein there is substantially no recirculation of the volumes of liquid in the chambers of the apparatus.

Preferably, the small volume is less than about 5 mL, preferably about 2 mL or less. The invention is particularly suitable for separating samples of about 0.02 mL to about 0.1 mL.

The sample is suitably any sample which contains compounds that need to be separated or treated. Examples include, but not limited to, blood-derived products such as plasma, antibody samples, samples containing biomolecules such as proteins, peptides, glycoproteins, oligonucleotides, recombinant proteins, cell extracts, cell culture supernatant, growth factors, antigens, immunogens, and combinations thereof.

Optionally, the electric potential is periodically stopping and reversed to cause movement of compounds having entered a separation membrane to move back into a sample chamber, while substantially not causing any compounds that have entered the separation chamber to re-enter sample chamber.

Reversal of current is an option but another alternative is a resting period. Resting (a period without an electric potential being applied) is an optional step that can replace or be included before or after an optional electrical potential reversal. This resting technique is often practised for protein separation work as an alternative to reversing the potential.

In order that the present invention may be more clearly understood, preferred forms will be described with reference to the following drawings and examples.

Now turning to the specific embodiments of the invention and referring to the drawings, FIG. 1 is a schematic view illustrating an electrolytic cell 10. The cell consists of two electrode compartments 11, 12, and one chamber 13 having a small volume, specifically cathode and anode compartments 11, 12 and sample chamber 13. A cathode 15 is located in cathode compartment 11 and a anode 16 is located in anode compartment 12. A restriction membrane 17 separates the sample chamber 13 from the cathode compartment 11 containing the cathode 15. Another restriction membrane 18 separates the sample chamber 13 from the anode compartment 12 which contains the anode 16. In use, the electrode compartments 11, 12 contain buffer and the restriction membranes 17, 18 defines holes or pores which are large enough to allow the flow of ions, but not large enough to allow the flow of large molecular mass compounds. A sample is applied to the sample chamber 13 by any suitable means and a voltage or electric potential is applied between the electrodes 15, 16 causing movement of salts and small molecular mass components out of the sample chamber 13 through the restriction membranes 17, 18 to the electrode compartments 11, 12.

It will be appreciated that the configuration of cathode and anode are suitably interchanged in any apparatus according to the present invention. The cathode is positioned above the anode in the drawings only for convenience. The polarity of the electrodes is simply be reversed by changing connections or reversing the polarity of the power source used to provide the electric potential.

Figure 2:
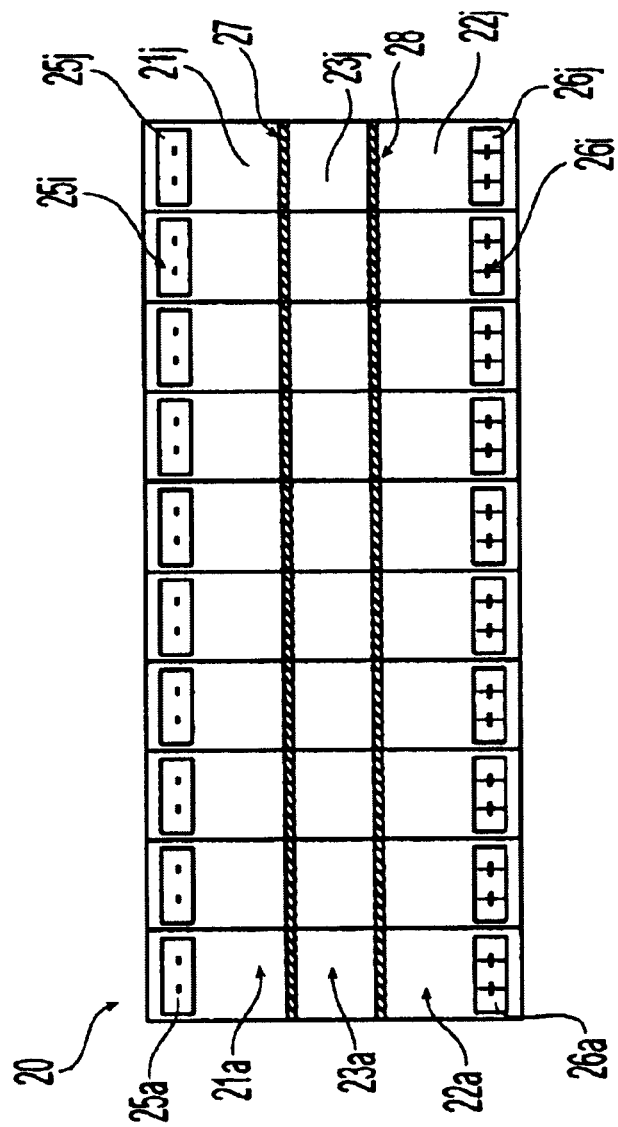
FIG. 2 is a schematic drawing illustrating the basic principal of the second aspect of the present invention having three membranes forming a number of compartments and chambers.

FIG. 2 shows a further variant of the arrangement shown in FIG. 1 in which instead of one anode compartment, one cathode compartment and a single sample chamber, the electrode compartment is divided up in to ten separate cathode compartments 21a–21j and ten separate anode compartments 22a–22j. Each electrode compartment has its own electrode 25a–25j and 26a–26j. Furthermore, the sample chamber is divided into a series of ten sample chambers 23a–23j. This arrangement allows treatment of ten small samples to be carried out under different buffer conditions at the same time. It is to be noted that each separation chamber pair suitably has different buffers or the same buffers. Each sample chamber 23a–23j has the same restriction membranes 27, 28.

Figure 3:
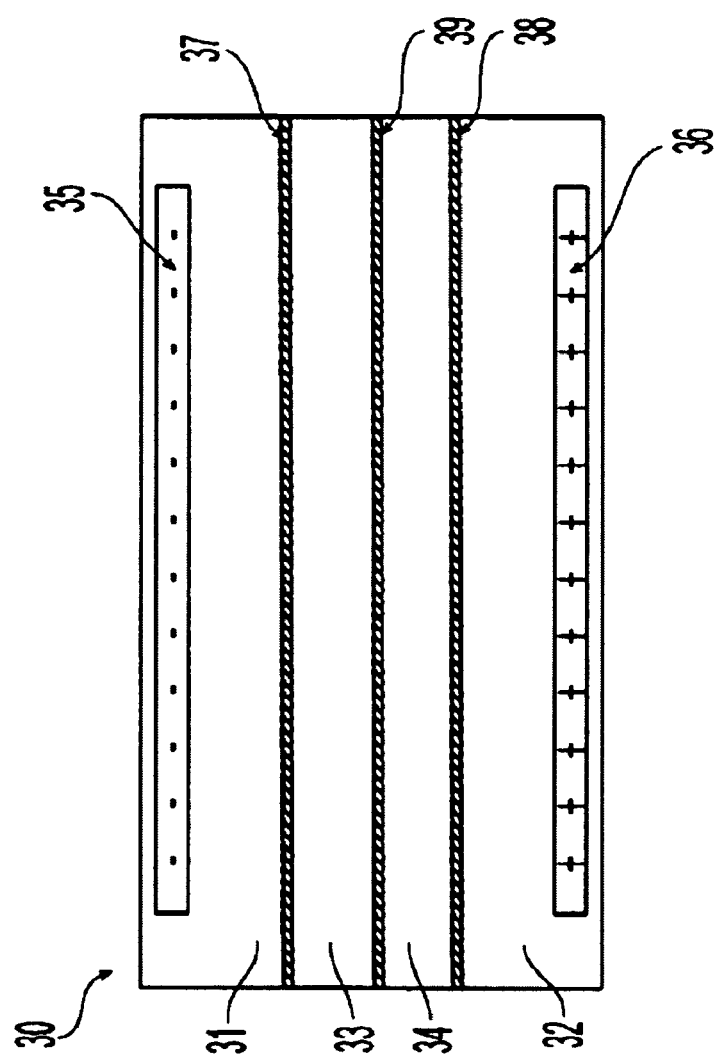
FIG. 3 is a schematic drawing illustrating a variant of the second aspect of the present invention.

FIG. 3 is a schematic view illustrating an electrolytic cell 30. The cell consists of two electrode compartments 31, 32 and two chambers 33, 34, specifically cathode and anode compartments 31, 32 and sample chamber 33 and separation chamber 34. A cathode 35 is located in cathode compartment 31 and a anode 36 is located in anode compartment 32. A restriction membrane 37 separates the sample chamber 33 from the cathode compartment 31 containing the cathode 35. Another restriction membrane 38 separates the separation chamber 34 from the anode compartment 32 which contains the anode 36. A separation membrane 39, separates the sample chamber 33 from the separation chamber 34. In use, the electrode compartments contain buffer and the restriction membrane are comprised of holes or pores which are large enough to allow the flow of ions, but not large enough to allow the flow of compounds. In use, a sample is applied to the sample chamber 33 by any suitable means and a voltage or electric potential applied between the electrodes 35, 36 causing movement of compounds out of the sample chamber 33 through the separation membrane 39 to the separation chamber 34.

There is no flow or recirculation of the contents of the sample or separation chambers or the electrode compartments. Samples in the sample and separation chambers remain essentially static, although clearly there will be some random movement of individual molecules, and also transfer of molecules across the restriction and separation membranes due to the electric field generated by the electrodes from mechanisms described above.

Figure 4:
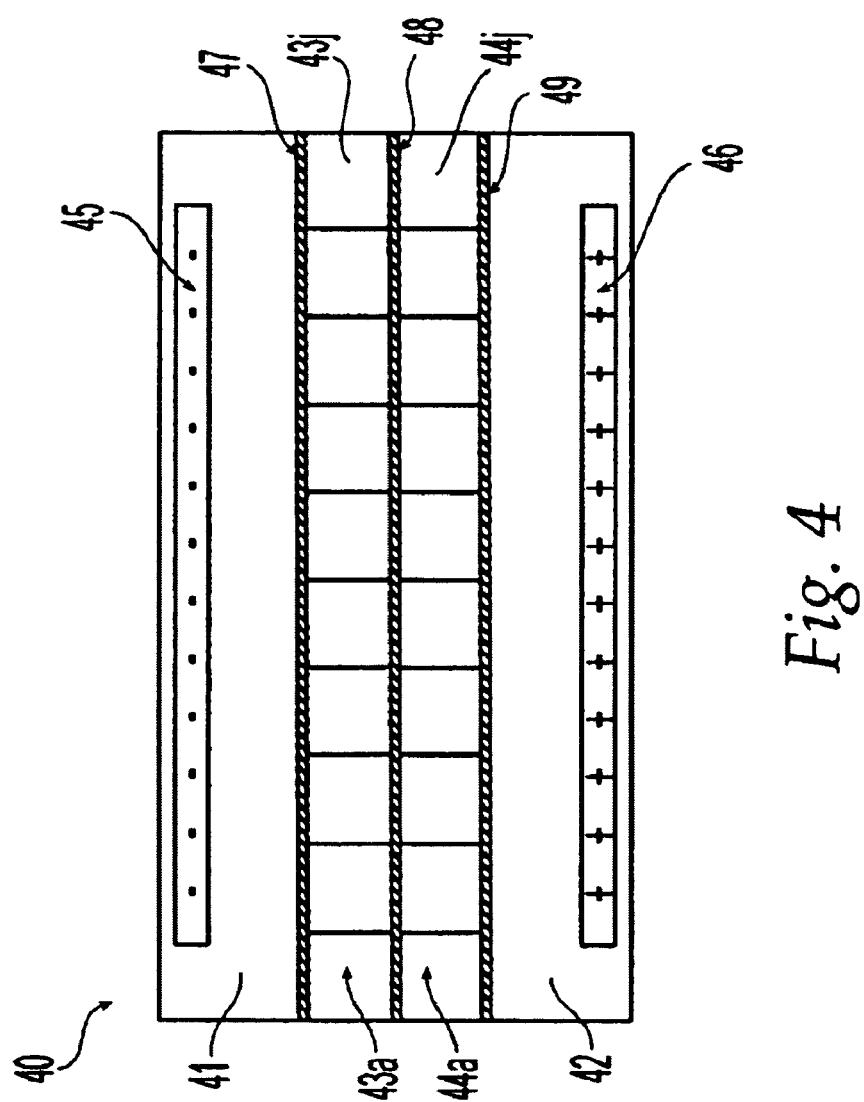
FIG. 4 is a schematic drawing illustrating an other variant of the basic principal shown in FIG. 3 having a plurality of chambers.

FIG. 4 shows a variant of the arrangement shown in FIG. 3 in which instead of a single sample chamber and separation chamber on either side of the separation membrane, the sample chamber is divided into a series of ten sample chambers 43a–43j and the separation chamber is divided into a series of ten separation chambers 44a–44j. This arrangement allows separations of ten small samples to be carried out at the same time. It is to be noted that each sample and separation chamber share the same buffer. The cell 40 also consists of cathode compartment 41, anode compartment 42, cathode 45 located in the cathode compartment, and anode 46 located in the anode compartment. Each sample chamber 43a–43j and each separation chamber 44a–44j have the same restriction membranes 47, 49 and the same separation membrane 48.

Figure 5:
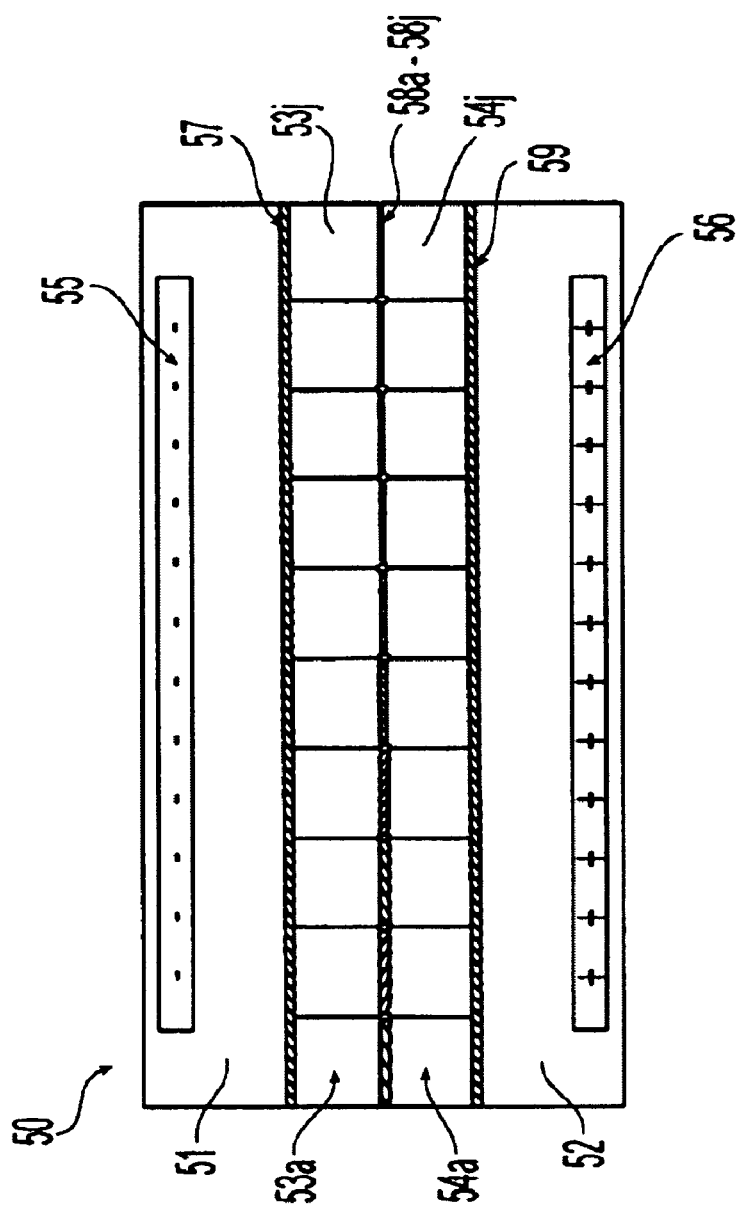
FIG. 5 is a schematic drawing illustrating an other variant of the basic principal shown in FIG. 3 having a plurality of chambers with a number of different separation membrane types for each chamber.

FIG. 5 shows a variant of the arrangement shown in FIG. 4 in which instead of a single separation membrane type, each sample 53a–53j and separation chamber 54a–54j pair has a different separation membrane 58a–58j. This arrangement allows up to ten different separations of ten small samples to be carried out at the same time. The cell 50 also consists of cathode compartment 51, anode compartment 52, cathode 55 located in the cathode compartment, and anode 56 located in the anode compartment. Each sample chamber 53a–53j and each separation chamber 54a–54j have the same restriction membranes 57, 59.

Figure 6:
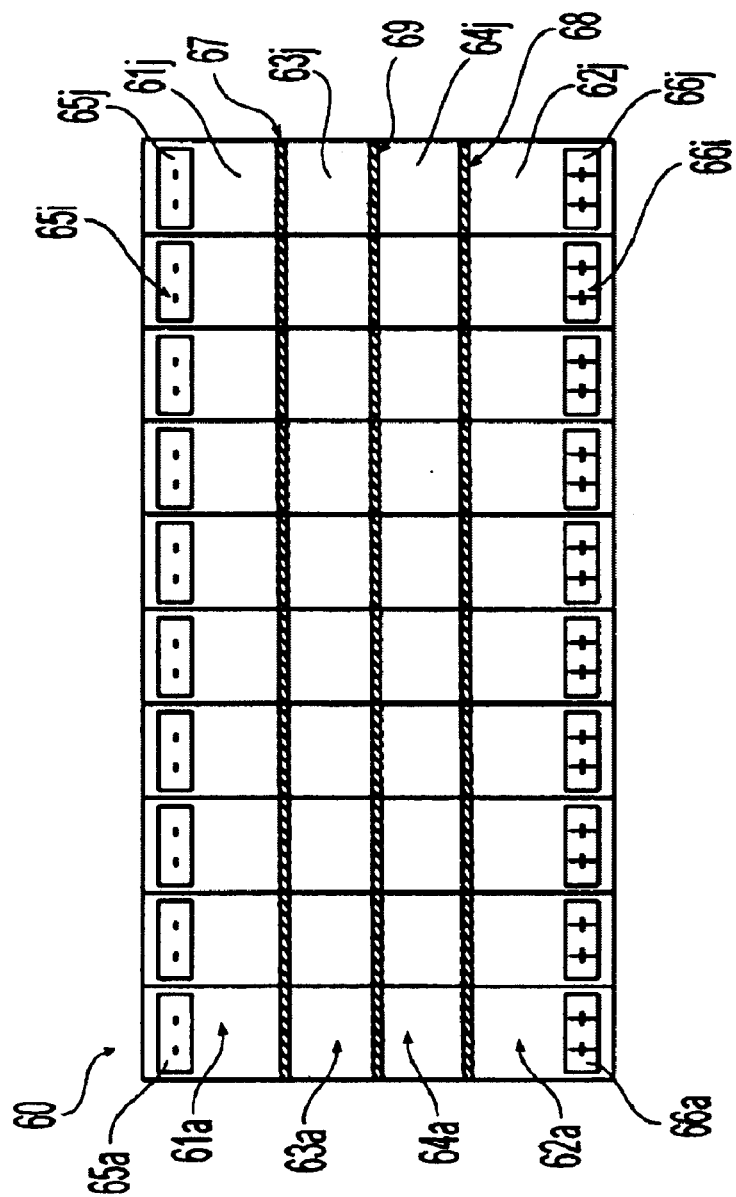
FIG. 6 is a schematic drawing illustrating a further variant of the second aspect of the present invention having a plurality of compartments and chambers.

FIG. 6 shows a further variant of the arrangement shown in FIG. 3 in which instead of one cathode compartment, one anode compartment, a single sample chamber and a single separation chamber either side of the separation membrane, the electrode compartments of the cell 60 are divided up in to ten separate cathode compartments 61a–61j and ten separate anode compartments 62a–62j. Each cathode compartment has its own cathode 65a–65j and each anode compartment has its own anode 66a–66j. Furthermore, the sample chamber is divided into a series of ten sample chambers 63a–63j and the separation chamber is divided into a series of ten separation chambers 64a–64j. This arrangement allows separations of ten small samples to be carried out under different buffer conditions at the same time. It is to be noted that each separation and sample chamber pair suitably have different buffers, the same buffers, or a combination thereof. Each sample chamber 63a–63j and each separation chamber 64a–64j have the same restriction membranes 67, 69 and the same separation membrane 68.

Figure 7:
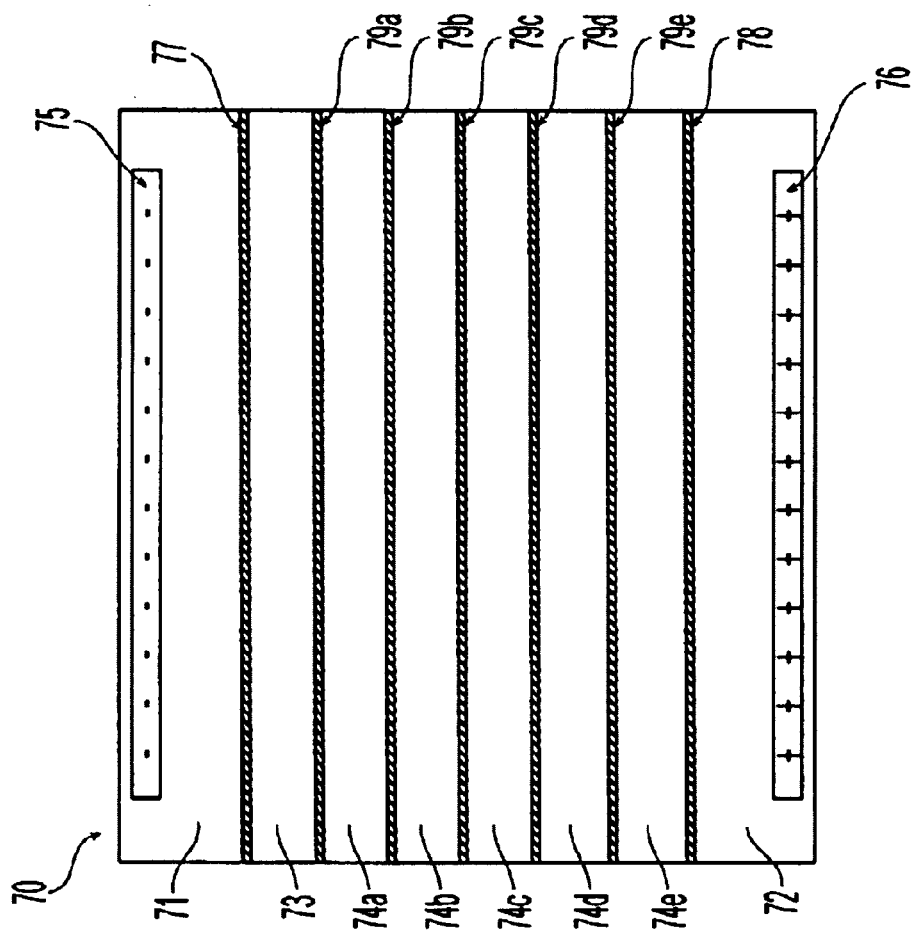
FIG. 7 is a schematic drawing illustrating a further variant of the second aspect of the present invention having seven membranes forming six chambers.

FIG. 7 is a schematic arrangement showing multiple separation chambers 74a–74e separated from each other by different separation membranes 79a–79e. In one preferred configuration, the separation membranes have decreasing molecular mass cutoffs proceeding further from the sample chamber 73. In this configuration, it is possible to separate a complex compound mixture in the sample chamber into different molecular masses defined by the various separation membranes. The cell 70 is also comprised of cathode compartment 71, anode compartment 72, cathode 75 located in the cathode compartment, anode 76 located in the anode compartment, and restriction membranes 77, 78 separating the sample chamber and the separation chambers from the electrode compartments.

Figure 8:
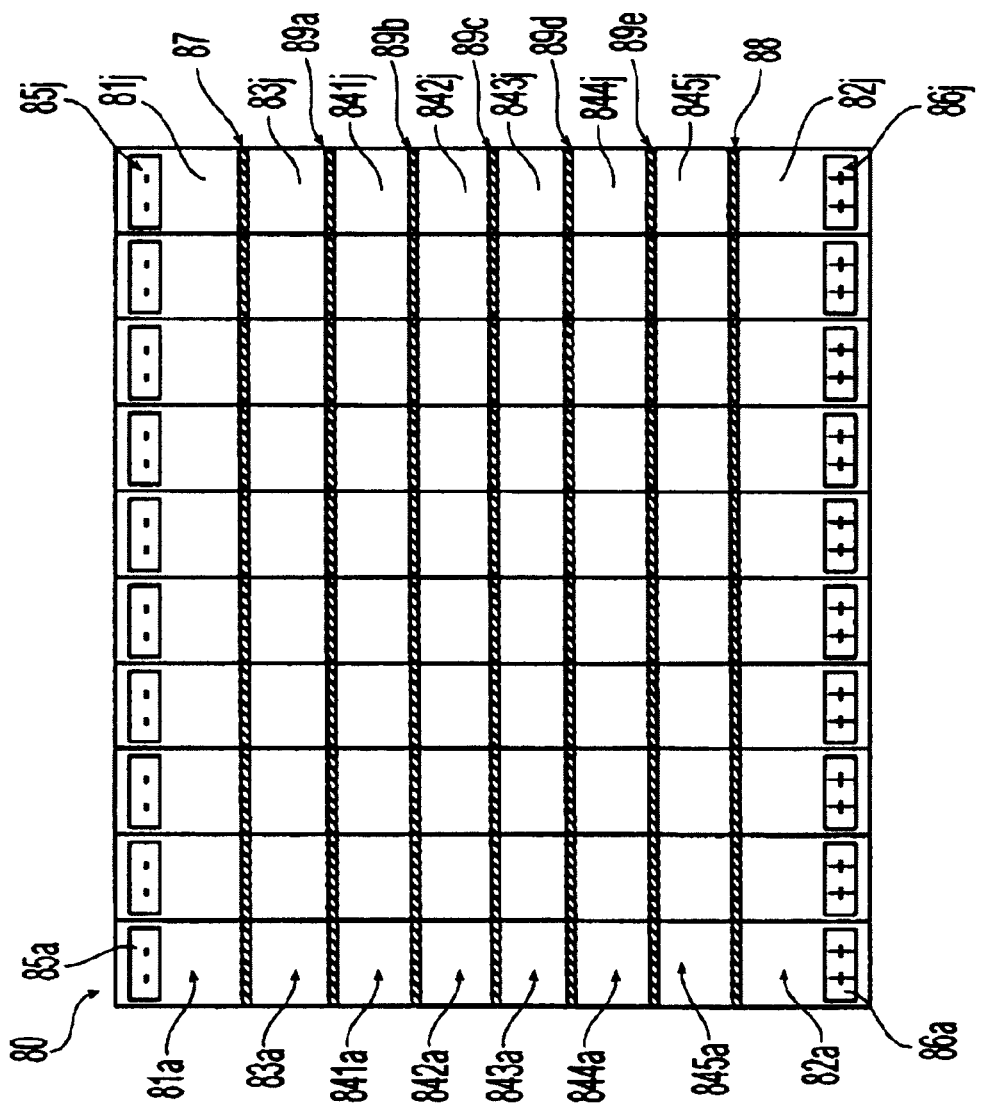
FIG. 8 is a schematic drawing illustrating a further variant of the second aspect of the present invention shown in FIG. 7 having a plurality of compartments and chambers.

FIG. 8 is a schematic arrangement showing an embodiment based on FIG. 7 but having multiple sample chambers 83a–83j and separation chambers 841a–841j, 842a–842j, 843a–843j, 844a–844j, and 845a–845j. In this configuration, it will be possible to carry out two-dimensional separation of compounds, using charge and molecular weight as variables. The cell 80 is also comprised often separate cathode compartments 81a–81j, ten separate anode compartments 82a–82j, ten separate cathodes 85a–85j located in the respective cathode compartments, and ten separate anodes 86a–86j located in the respective anode compartments. Restriction membranes 87, 88 separating the sample chambers and the separation chambers from the electrode compartments.

In this arrangement, it will be possible to determine the pI of a given protein by determining movement of the protein through the various separation membranes having decreasing molecular mass cut-offs at different pHs. In this situation, electrophoresis is carried out in buffers having increasing pH from the left hand side through to the right hand side of the apparatus. After electrophoresis, the separation chamber that contains the protein which has first moved through the membranes having molecular mass cut-offs greater than the protein would be indicative of the pI of the protein. It is also be possible to carry out multiple separations under different buffers to determine which proteins moved through to the separation chambers under varying pH conditions.

Figure 9:
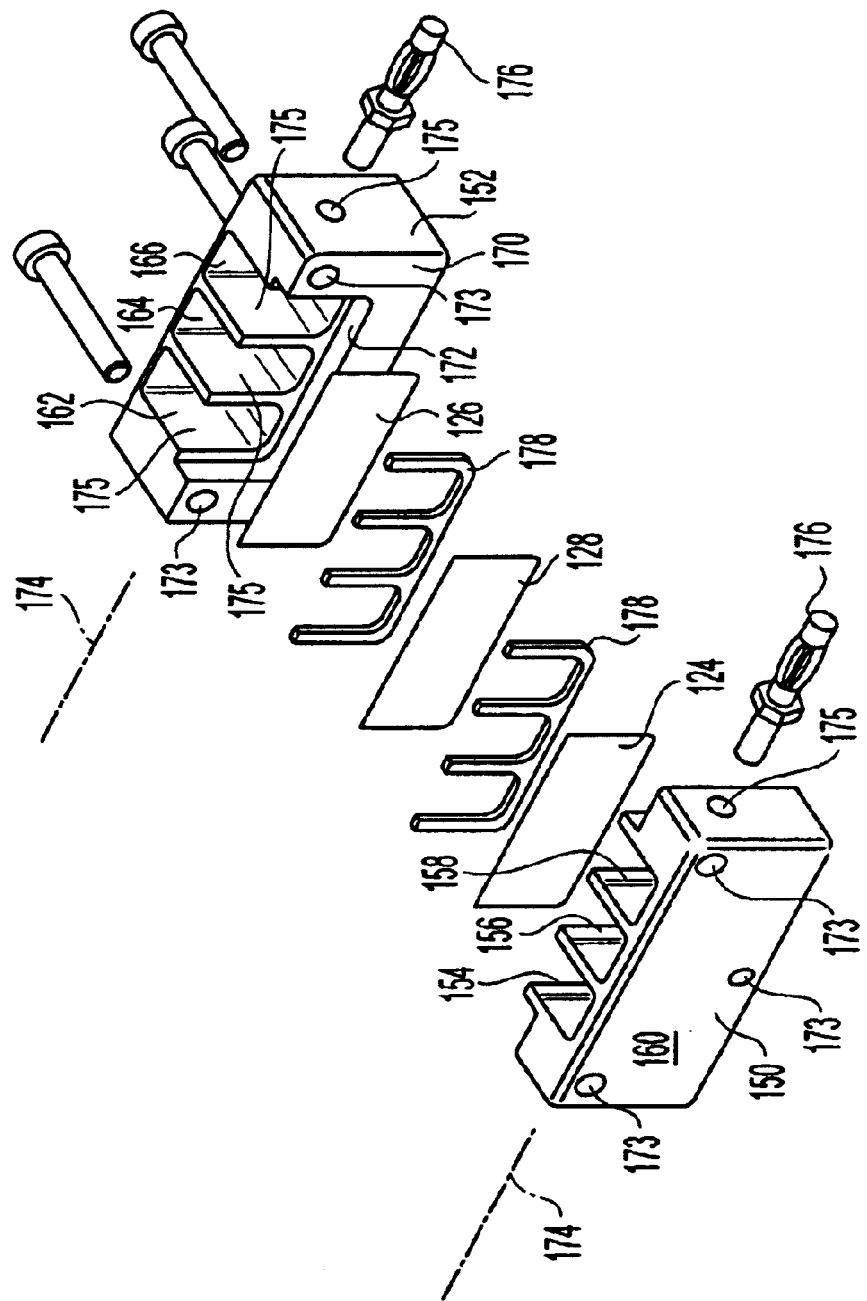
FIG. 9 is an exploded view of an apparatus embodying the present invention.

FIG. 9 shows an exploded view of a physical embodiment of an apparatus 100 according to the present invention. The apparatus comprises two body portions 150 and 152. There are three generally U-shaped channels 154, 156, 158 which extend from a rear wall 160 of the first body portion 150 to the front of the body portion. The three channels 154, 156, 158 are contiguous and parallel, and channels 154 and 156 share a side wall as do channels 156 and 158. The end walls of the group of three channels terminate in a plane which projects from the front wall of the first body portion 150.

The second body portion 152 also provides three channels 162, 164, 166 which extend from its rear wall 168. Those channels are also contiguous and channels 162 and 164 share a side wall as do channels 164 and 166. The cross-section of the three channels 162, 164, 166 matches that of channel 154, 156, 158. The end walls of the group of three channels define a recess 172 which is of a size and shape to receive the end walls of the projecting channels from body portion 150 with a small amount of clearance. When the two body portions 150, 152 are pushed together the end walls of the channels do not meet but are spaced apart by a relatively small distance of several millimeters. The gap between the end walls forms a space in which the sample and separation chambers are located. The channels define the outer compartments which hold the buffer.

Three through holes 173 are provided in each body portion, one either side of the channels and one below the channels which are aligned so that when the holes are aligned and the left and right hand blocks join together, the three channels in the block 152 align with the three channels in the block 150 and their ends locate in the recess 172.

A hole 175 extends transversely across each body portion through the walls of the channels. Both holes receives a platinum wire 174 which is connected to a terminal 176.

An arrangement of chambers similar to that illustrated in FIG. 3 but having only three sample chambers and separation chambers is provided in the space between the end walls. The chambers are provided by a sandwich construction of a restriction membrane 124, a grid spacer element 178 of the same cross section as the groups of channels, a separation membrane 128, a further grid spacer 178 and a further restriction membrane 126.

An important feature of the apparatus shown, apart from the lack of flow/circulation and the lack of a pump, is that both the cathode and anode compartments and the separation and sample chambers are all top loading. That means that the samples and the buffer solution is simply injected or otherwise dropped into the relevant compartments and chambers from above using a syringe or pipette or the like. This makes the apparatus easy to use compared with the traditional electrophoresis apparatus where the separation membrane tends to be aligned in a horizontal plane in use, rather than a vertical plane and sample loading is more complex.

Figure 11:
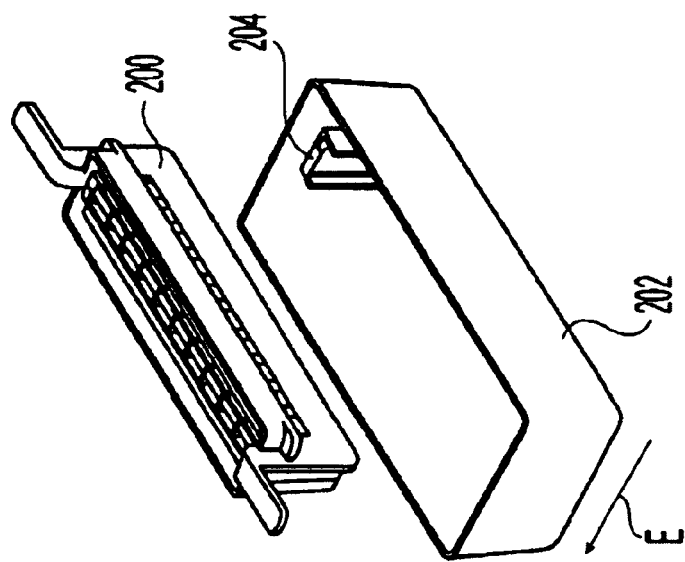
FIG. 11 is an assembled view of the embodiment of FIG. 10.
Figure 10:
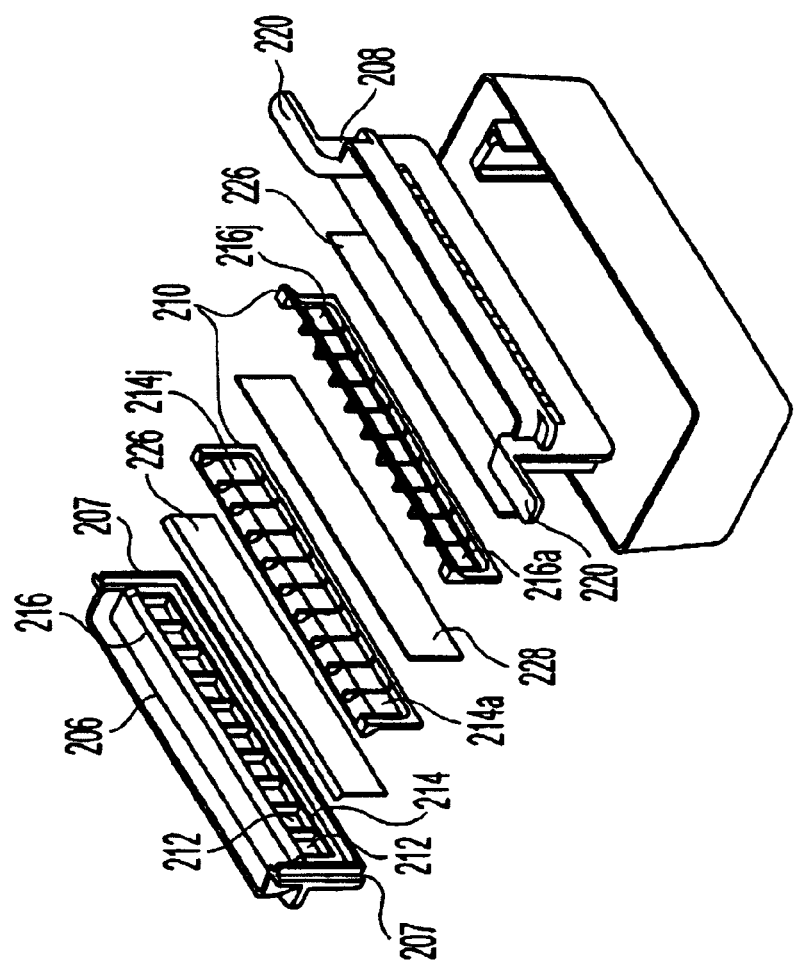
FIG. 10 is an exploded view of a second embodiment of the present invention.

FIGS. 10 and 11 illustrate a further embodiment of an apparatus according to the present invention incorporating a removable cartridge 200, which optionally, is disposable. In this embodiment, a separate buffer tank 202 is provided which includes electrodes, not shown, which provide an electric field E passing transversely across the tank as shown by the arrow E. At each longitudinal end of the tank, there is provided a female engagement means 204 of which only one is visible in FIGS. 10 and 11, between which the cartridge housing is suitably engaged in a sliding arrangement.

The cartridge 200 comprises a number of components including, two mating housing components, a male component 206 and a female component 208, which are adapted to receive two restriction membranes 226, two grids 210 defining a well structure and a separation membrane 228.

The male cartridge housing component 206 is generally rectangular in cross section and defines a generally U shaped rib 207 which projects outwardly from the sides and base of the housing component. The rib mates in a corresponding recess, not shown, which is defined in the sides and the base of the female housing component. A series of holes 212 extend through the male cartridge housing component from an outer face which is hidden in FIGS. 10 and 11 to an inner face 214. The holes are generally rectangular. The inner face 214 of the housing component is recessed relative to the projecting rib so as to define a recess for receiving the restriction membrane 226 and the grid 210. The top 216 of the recess is chamfered and slopes away towards the outside of the housing. The upper part of the restriction membrane 226 is also bent to match the angle of chamfer of the recess in the housing component.

The grid defining a well structure is an insert which fits inside the recess in the male housing component. The grid defines a series of ten contiguous well structures or chambers 214a–214j which in use are the sample chambers and which are aligned with the ten apertures defined in the cartridge housing components. The upper end of the well structure is open. At the top of the wells, there is a beveled portion which extends outwardly and matches the chamfer of the top of the recess of the housing component, so that the outer face of the well structure matches the inner face of the cartridge housing and restriction membrane.

The female cartridge housing component is largely a mirror image of the male cartridge housing component apart from the U shaped channel which receives the rib in a snap fit action to lock the male housing to the female housing. The female housing receives an identical restriction membrane and grid to the male housing, the grid defining the separation chambers 216a–216j. Also the female housing defines two handles which extend upwardly and outwardly from the cartridge. The cartridge will be typically made in a plastics material and is ideally made sufficiently cheaply that it is disposable, although it would in theory be possible to re-use the cartridge if the cartridge were properly cleaned and the separation membrane removed and replaced after use.

It is to be noted that the upper part of the well structure is wider than the lower part of the well structure so that it acts as a type of funnel which makes it easier to load a sample into the chambers of the well structure. This allows the lower part of the chamber to be narrow so that the sample size can be very small and so that the separation process occurs rapidly due to the small sample size.

The embodiment shown in FIGS. 10 and 11 has advantages in ease of use over the embodiment shown in FIG. 9, although unlike the embodiment shown in FIG. 9, it has the restriction that all the separation and sample chambers share the same buffer.

The apparatus and method of the present invention is suitably also applied to dialysis in which case no separation membrane is used, and the sample and separation or sample and separation chambers form one sample chamber. This arrangement is shown in FIG. 1 with FIG. 2 illustrating a schematic arrangement showing multiple dialysis with multiple electrode compartments and multiple sample chambers. The positive and negative electrodes may be connected together so that the electric field across the multiple electrode compartments and sample chambers is uniform or alternatively, the electrodes could be insulated from one another and used to provide differing electric fields across the differing chambers.

A real advantage of the present invention is the ability to load very small samples and carry out fast separations without significant loss of the proteins or undue dilution of the samples. The ability to carry out dialysis of very small samples is also a distinct advantage for the same reasons.

Figure 12:
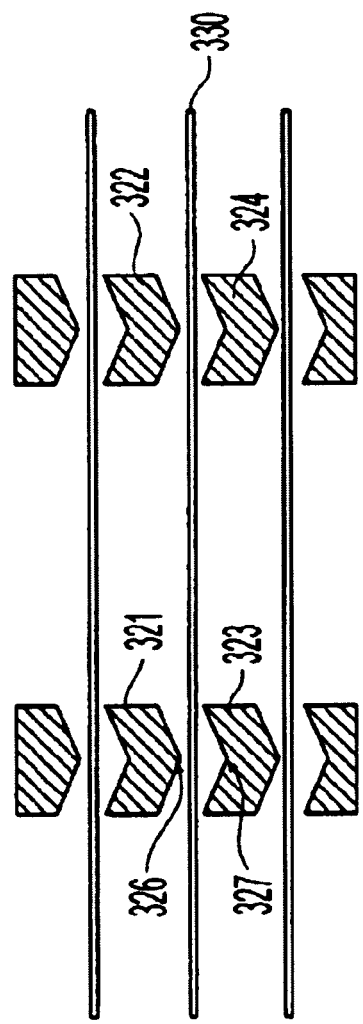
FIG. 12 is a schematic drawing illustrating sealing means for the membranes during assembly of an apparatus according to the present invention.

FIG. 12 shows a means for sealing membranes in an apparatus according to the present invention having multiple sample and separation chambers. Seals 321, 322 are compressed against seals 323 and 324 with membrane 330 positioned therebetween. The membrane is compressed between areas 326 and 327 of seals 321 and 323 respectively.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

What we claim is:

1. An electrophoresis apparatus for processing compounds in small sample volumes comprising:
   (a) a cathode in a static cathode buffer zone or compartment;
   (b) an anode in a static anode buffer zone or compartment, the cathode disposed relative to the anode so as to be adapted to generate an electric field in an electric field area therebetween upon application of a voltage potential between the cathode and anode;
   (c) a removable cartridge disposed in the electric field area between the anode and cathode, the cartridge containing a first non-isoelectric separation barrier and a second non-isoelectric separation barrier disposed between a selected one of the cathode buffer zone and the anode buffer zone and the first barrier so as to define a first chamber having an interstitial volume of less than 5 mL therebetween;
   wherein in use, the removable cartridge containing the non-isoelectric separation barriers is disposed in the apparatus forming the cathode buffer zone and the anode buffer zone, electrophoretic buffer is disposed in the cathode buffer zone and the anode buffer zone, a sample containing one or more compounds is provided to the first chamber; wherein upon application of the voltage potential a selected compound is removed from the sample through one of the first or second non-isoelectric separation barriers and provided to one of the cathode buffer zone or the anode buffer zone; and wherein there is substantially no circulation of buffer or sample in the buffer zones or the first chamber.

2. The apparatus according to claim 1 wherein the interstitial volume is less than or equal to about 2 mL.

3. The apparatus according to claim 2 wherein the interstitial volume is from about 0.02 mL to about 0.1 mL.

4. The apparatus according to claim 1 wherein a ratio of interstitial volume to barrier surface area in the chamber is less than about 1 mL/cm$^2$.

5. The apparatus according to claim 1 wherein the ratio of interstitial volume to barrier surface area in the chamber is less than or equal to about 0.5 mL/cm$^2$.

6. The apparatus according to claim 1 wherein the ratio of interstitial volume to barrier surface area in the chamber is less than or equal to about 0.1 mL/cm$^2$.

7. The apparatus according to claim 1 wherein the ratio of interstitial volume to barrier surface area in the chamber is about 0.02 mL/cm$^2$.

8. The apparatus according to claim 1 wherein the first and second barriers are non-isoelectric membranes selected from the group consisting of electrophoresis separation membranes having a defined pore size or restriction membranes which allow flow of ions into and out of a chamber or compartment under the influence of an electric field but do not allow movement of macromolecules, or a combination thereof.

9. The apparatus according to claim 8 wherein at least one of the first and second membranes is an ion-permeable electrophoresis separation membrane comprised of polyacrylamide and having a molecule mass cut-off from about 1 kDa to about 1500 kDa.

10. The apparatus according to claim 9 wherein a selected one of the first and second membranes is an ion-permeable electrophoresis separation membrane comprised of polyacrylamide and having a molecule mass cut-off from about 1 kDa to about 1500 kDa and the other membrane is a restriction membrane comprised of polyacrylamide and having a molecular mass cut-off less than the separation membrane.

11. The apparatus according to claim 1 wherein the first and second separation barriers are non-isoelectric membranes comprised of materials selected from the group consisting of ultrafiltration materials, electrodialysis materials, haemodialysis materials, and combinations thereof.

12. The apparatus according to claim 1 comprising a plurality of separation membranes space apart defining a plurality of chambers having an interstitial volume of less than 5 mL.

13. A method for de-salting or dialysing a small volume sample containing at least one compound and one or more salts comprising:
   (a) providing an apparatus according to claim 1;
   (b) adding buffer to the cathode and anode buffer zones or compartments;
   (c) placing a sample in the first chamber; and
   (d) applying a voltage potential, wherein upon application of the voltage potential, and one or more salts in the sample are removed from the sample through a selected one of the first and second separation barriers and provided to a selected one of the cathode buffer zone and the anode buffer zone, wherein at least one compound is substantially retained in the first chamber, and wherein there is substantially no circulation of buffer or sample in the buffer zones and the first chamber.

14. A method of separating a compound in a small sample volume by electrophoretic separation comprising:
   (a) providing an apparatus according to claim 1;
   (b) adding buffer to the cathode and anode buffer zones or compartments;
   (c) placing a sample containing one or more compounds in the first chamber; and
   (d) applying a voltage potential, wherein upon application of the voltage potential, a compound in the sample is removed from the sample through a selected one of the first and second separation barriers and provided to a selected one of the cathode buffer zone and the anode buffer zone, wherein at least one compound is substantially retained in the first chamber, and wherein there is substantially no circulation of buffer or sample in the buffer zones and the first chamber.

15. An electrophoresis apparatus for processing compounds in small sample volumes comprising:
   (a) a cathode in a static cathode buffer zone or compartment;
   (b) an anode in a static anode buffer zone or compartment, the cathode disposed relative to the anode so as to be adapted to generate an electric field in an electric field area therebetween upon application of a voltage potential between the cathode and anode;

(c) a removable cartridge disposed in the electric field area between the anode and cathode, the cartridge comprising a first non-isoelectric separation barrier;

a second non-isoelectric separation barrier disposed between the cathode buffer zone and the first barrier so as to define a first chamber having an interstitial volume of less than 5 mL therebetween;

and also a third non-isoelectric separation barrier disposed between the anode buffer zone and the first barrier so as to define a second chamber having a interstitial volume of less than 5 mL therebetween;

wherein in use, the removable cartridge containing the non-isoelectric separation barriers is disposed in the apparatus forming the cathode buffer zone and the anode buffer zone, electrophoretic buffer is disposed in the cathode buffer zone, the anode buffer zone and at least one of the first and second chambers, a sample containing one or more compounds is provided to a selected one of the first and second chambers; wherein upon application of the voltage potential, a selected compound is removed from the sample through the first separation barrier, and provided to the other of the first and second chambers; and wherein there is substantially no circulation of buffer or sample in the buffer zones, the first chamber or the second chamber.

16. The apparatus according to claim 15 wherein the interstitial volume is less than or equal to about 2 mL.

17. The apparatus according to claim 16 wherein the interstitial volume is from about 0.02 mL to about 0.1 mL.

18. The apparatus according claim 15 wherein a ratio of interstitial volume to barrier surface area in a chamber is less than about 1 mL/cm$^2$.

19. The apparatus according to claim 18 wherein the ratio of interstitial volume to barrier surface area in a chamber is less than or equal to about 0.5 mL/cm$^2$.

20. The apparatus according to claim 19 wherein the ratio of interstitial volume to barrier surface area in a chamber is less than or equal to about 0.1 mL/cm$^2$.

21. The apparatus according to claim 20 wherein the ratio of sample volume to barrier surface area in a chamber is about 0.02 mL/cm$^2$.

22. The apparatus according to claim 15 wherein the first separation barrier is an electrophoresis membrane having a defined pore size and the second and third separation barriers are restriction membranes which allow flow of ions into and out of a chamber or compartment under the influence of an electric field.

23. The apparatus according to claim 22 wherein the separation membrane is an ion-permeable electrophoresis separation membrane comprised of polyacrylamide and having a molecule mass cut-off from about 1 kDa to about 1500 kDa.

24. The apparatus according to claim 22 wherein the restriction membrane is comprised of polyacrylamide and having a molecular mass cut-off less than the separation membrane.

25. The apparatus according to claim 15 wherein the first, second and third separation barriers are membranes comprised of materials selected from the group consisting of ultrafiltration materials, electrodialysis materials, haemodialysis materials, and combinations thereof.

26. The apparatus according to claim 15 wherein at least a fifth separation barrier is disposed between the third separation barrier and the anode buffer zone to define at least a third chamber having an interstitial volume of less than 5 mL, wherein the sample is provided to the first chamber, wherein upon application of the voltage potential, a selected compound is removed from the sample through the separation barriers, and provided to selected chamber.

27. A method for de-salting or dialysing a small volume sample containing at least one compound and one or more salts comprising:

(a) providing an apparatus according to claim 15;

(b) adding buffer to the cathode and anode buffer zones or compartments and to at least one of the chambers;

(c) placing a sample in a selected one of the first and second chambers; and (d) applying a voltage potential between the first and second chambers, wherein upon application of the voltage potential, and one or more salts in the sample are removed from the mixture through a selected one of the first separation barrier and provided to the other of the first and second chamber, wherein at least one compound is substantially retained in first chamber from which the salt is removed, wherein there is substantially no circulation of buffer or sample in the buffer zones, the first chamber, and the second chamber.

28. A method of separating a compound in small sample volume by electrophoretic separation comprising:

(a) providing an apparatus according to claim 15;

(b) adding buffer to the cathode and anode buffer zones or compartments and to at least one of the chambers;

(c) placing a sample containing a mixture of two or more compounds in a selected one of the first and second chambers; and (d) applying a voltage potential between the first and second chambers, wherein upon application of the voltage potential, a first compound in the sample is removed from the mixture through a selected one of the first separation barrier and provided to the other of the first and second chamber, wherein a second compound is substantially retained in first chamber from which the first compound was removed, wherein there is substantially no circulation of buffer or sample in the buffer zones, the first chamber, and the second chamber.

29. An electrophoresis apparatus for processing compounds in small sample volumes comprising:

(a) a cathode in a static cathode buffer zone or compartment;

(b) an anode in a static anode buffer zone or compartment, the cathode disposed relative to the anode so as to be adapted to generate an electric field in an electric field area therebetween upon application of a voltage potential between the cathode and anode;

(c) a removable cartridge disposed in the electric field area between the anode and cathode, the cartridge comprising a first non-isoelectric separation barrier;

a second non-isoelectric separation barrier disposed between a selected one of the cathode buffer zone and the anode buffer zone and the first barrier so as to define a first chamber having an interstitial volume of less than 5 mL therebetween; and also a third non-isoelectric separation barrier disposed between the anode buffer zone an the first barrier so as to define a second chamber having an interstitial volume of less than 5 mL therebetween;

wherein in use, the removable cartridge containing the non-isoelectric separation barriers is disposed in the apparatus forming the cathode buffer zone and the anode buffer zone, electrophoretic buffer is disposed in the cathode buffer zone and the anode buffer zone, and at least one of the first chamber and second chamber, a sample containing one or more compounds is provided to the first chamber; wherein upon application of the voltage potential a selected compound is removed from the sample through the first or second non-isoelectric separation barriers and provided to the second chamber; and wherein there is substantially no circulation of buffer or sample in the buffer zones or the first chamber.

30. The apparatus according to claim 29 wherein a least a fourth separation barrier is disposed between the second separation barrier and the cathode buffer zone to define at least a third chamber having an interstitial volume less than about 5 mL, wherein sample is provided to a selected second and third chamber, wherein upon application of the voltage potential, a selected compound is removed from the sample through the separation barriers, and provided to the first chamber.

31. The apparatus according to claim 29 wherein at least a fifth separation barrier is disposed between the third separation barrier and the anode buffer zone to define at least a fourth chamber having an interstitial volume of less than 5 mL, wherein the sample is provided to selected chambers, wherein upon application of the voltage potential, a selected compound is removed from the sample through the separation barriers, and provided to a selected chamber.

32. The apparatus according to claim 31 wherein the apparatus further comprises at least a second cathode in a second static cathode buffer zone and a second anode in a second static anode zone disposed relative to the second cathode so as to be adapted to generate an electric field between a selected chamber and another selected chamber.

33. A method for de-salting or dialysing a small volume sample containing at least one compound and one or more salts comprising:
  (a) providing an apparatus comprising a cathode in a static cathode buffer zone or compartment; an anode in a static anode buffer zone or compartment, the cathode disposed relative to the anode so as to be adapted to generate an electric field in an electric field area therebetween upon application of a voltage potential between the cathode and anode; a first non-isoelectric separation barrier disposed in the electric field area; and a second non-isoelectric separation barrier disposed between a selected one of the cathode buffer zone and the anode buffer zone and the first barrier so as to define a first chamber having an interstitial volume of less than 5 mL between the first separation barrier and the second separation barrier;
  (b) adding buffer to the cathode and anode buffer zones or compartments;
  (c) placing a sample in the first chamber; and
  (d) applying a voltage potential wherein upon application of the voltage potential, one or more salts in the sample are removed from the sample through a selected one of the first and second separation barriers and provided to a selected one of the cathode buffer zone and the anode buffer zone, wherein at least one compound is substantially retained in the first chamber, and wherein there is substantially no circulation of buffer or sample in the buffer zones and the first chamber.

34. The method according to claim 33 wherein the interstitial volume is less than or equal to about 2 mL.

35. The method according to claim 34 wherein the interstitial volume is from about 0.02 mL to about 0.1 mL.

36. The method according to claim 33 wherein a ratio of interstitial volume to barrier surface area in the chamber is less than about 1 mL/cm$^2$.

37. The method according to claim 33 wherein the ratio of interstitial volume to barrier surface area in the chamber is less than or equal to about 0.5 mL/cm$^2$.

38. The method according to claim 33 wherein the ratio of interstitial volume to barrier surface area in the chamber is less than or equal to about 0.1 mL/cm$^2$.

39. The method according to claim 33 wherein the ratio of interstitial volume to barrier surface area in the chamber is about 0.02 mL/cm$^2$.

40. The method according to claim 33 wherein the first and second barriers are non-isoelectric membranes selected from the group consisting of electrophoresis separation membranes having a defined pore size or restriction membranes which allow flow of ions into and out of a chamber or compartment under the influence of an electric field but do not allow movement of macromolecules, or a combination thereof.

41. The method according to claim 40 wherein at least one of the first and second membranes is an ion-permeable electrophoresis separation membrane comprised of polyacrylamide and having a molecule mass cut-off from about 1 kDa to about 1500 kDa.

42. The method according to claim 33 wherein a selected one of the first and second membranes is an ion-permeable electrophoresis separation membrane comprised of polyacrylamide and having a molecule mass cut-off from about 1 kDa to about 1500 kDa and the other membrane is a restriction membrane comprised of polyacrylamide and having a molecular mass cut-off less than the separation membrane.

43. The method according to claim 33 wherein the first and second separation barriers are non-isoelectric membranes comprised of materials selected from the group consisting of ultrafiltration materials, electrodialysis materials, haemodialysis materials, and combinations thereof.

44. A method for de-salting or dialysing a small volume sample containing at least one compound and one or more salts comprising:
  (a) providing an apparatus comprising a cathode in a static cathode buffer zone or compartment; an anode in a static anode buffer zone or compartment, the cathode disposed relative to the anode so as to be adapted to generate an electric field in an electric field area therebetween upon application of a voltage potential between the cathode and anode; a first non-isoelectric separation barrier disposed in the electric field area; a second non-isoelectric separation barrier disposed between the cathode buffer zone and the first barrier so as to define a first chamber having an interstitial volume of less than 5 mL between the first separation barrier and the second separation barrier; and a third non-isoelectric separation barrier disposed between the anode buffer zone and the first barrier so as to define a second chamber having a interstitial volume of less than 5 mL between the third separation barrier and the first barrier;
  (b) adding buffer to the cathode and anode buffer zones or compartments and to at least one of the chambers;
  (c) placing a sample in a selected one of the first and second chambers; and
  (d) applying a voltage potential between the first and second chambers, wherein upon application of the voltage potential one or more salts in the sample are removed from the mixture through a selected one of the first separation barrier and provided to the other of the first and second chamber, wherein at least one compound is substantially retained in first chamber from which the salt is removed, wherein there is substantially no circulation of buffer or sample in the buffer zones, the first chamber, and the second chamber.

45. The apparatus according to claim 33 or 44 comprising a plurality of separation membranes space apart defining a plurality of chambers each having an interstitial volume of less than 5 mL.

* * * * *